US012605189B2

(12) United States Patent
Gray et al.

(10) Patent No.: US 12,605,189 B2
(45) Date of Patent: Apr. 21, 2026

(54) ORTHOPEDIC SCREW EXTENSION

(71) Applicant: MiRus LLC, Marietta, GA (US)

(72) Inventors: Wayne Gray, Marietta, GA (US); Jay Yadav, Marietta, GA (US)

(73) Assignee: MiRus LLC, Marietta, GA (US)

( * ) Notice: Subject to any disclaimer, the term of this patent is extended or adjusted under 35 U.S.C. 154(b) by 474 days.

(21) Appl. No.: 18/098,510

(22) Filed: Jan. 18, 2023

(65) Prior Publication Data

US 2023/0225766 A1 Jul. 20, 2023

Related U.S. Application Data

(63) Continuation-in-part of application No. 29/855,227, filed on Sep. 30, 2022, now Pat. No. Des. 1,045,082.

(60) Provisional application No. 63/300,318, filed on Jan. 18, 2022.

(51) Int. Cl.
| | | |
|---|---|---|
| *A61B 17/70* | (2006.01) | |
| *A61B 17/00* | (2006.01) | |
| *A61B 17/86* | (2006.01) | |

(52) U.S. Cl.
CPC ...... *A61B 17/7032* (2013.01); *A61B 17/8685* (2013.01); *A61B 2017/00477* (2013.01)

(58) Field of Classification Search
CPC ............ A61B 17/7049; A61B 17/8685; A61B 17/7032; A61B 17/7034; A61B 17/7035; A61B 17/7037; A61B 17/8605; A61B 17/7001; A61B 17/00477
See application file for complete search history.

(56) References Cited

U.S. PATENT DOCUMENTS

| | | | | |
|---|---|---|---|---|
| 7,635,380 | B2 * | 12/2009 | Zucherman | ........ A61B 17/7035 |
| | | | | 606/267 |
| 7,909,859 | B2 | 3/2011 | Mosca et al. | |
| 8,231,662 | B2 | 7/2012 | Huebner | |
| 8,343,200 | B2 | 1/2013 | Khanna et al. | |
| 8,574,268 | B2 | 11/2013 | Chan et al. | |
| 8,663,289 | B2 | 3/2014 | Schwab | |
| 8,727,972 | B2 | 5/2014 | Zhang et al. | |
| 8,734,493 | B2 | 5/2014 | Kirschman | |
| 8,845,640 | B2 | 9/2014 | McLean et al. | |
| 8,906,076 | B2 | 12/2014 | Mocanu et al. | |
| 9,198,698 | B1 | 12/2015 | Doose et al. | |
| 9,247,975 | B2 | 2/2016 | Erhart et al. | |
| 9,615,869 | B2 | 4/2017 | Brown et al. | |
| 10,258,380 | B2 | 4/2019 | Sinha | |
| 10,327,822 | B2 | 6/2019 | Austin et al. | |
| 10,376,290 | B2 | 8/2019 | Courtney et al. | |
| 10,441,334 | B2 | 10/2019 | Horwitz | |
| 10,743,922 | B1 | 8/2020 | Touchet et al. | |
| 10,835,302 | B2 | 11/2020 | Gonzalez-Hernandez | |
| 10,888,358 | B2 | 1/2021 | Perrow et al. | |
| 10,898,251 | B2 | 1/2021 | Fallin | |
| 11,058,461 | B2 * | 7/2021 | Zhang | ................ A61B 17/8685 |
| 11,241,258 | B2 * | 2/2022 | Raju | ................. A61B 17/7032 |
| 11,547,453 | B2 * | 1/2023 | Lengyel | ............ A61B 17/7041 |
| 12,144,523 | B2 * | 11/2024 | Palagi | ................ A61B 17/8605 |
| 2009/0099605 | A1 | 4/2009 | Fallin et al. | |

(Continued)

*Primary Examiner* — Eduardo C Robert
*Assistant Examiner* — Holly Joanna Lane
(74) *Attorney, Agent, or Firm* — UB Greensfelder LLP; Brian E. Turung

(57) ABSTRACT

An orthopedic screw extension for use in spinal implant applications.

15 Claims, 6 Drawing Sheets

(56)     References Cited

U.S. PATENT DOCUMENTS

| | | | |
|---|---|---|---|
| 2010/0160981 A1* | 6/2010 | Butler ................ | A61B 17/7049 |
| | | | 606/308 |
| 2011/0106178 A1* | 5/2011 | Schwab ............. | A61B 17/7037 |
| | | | 606/305 |
| 2018/0317972 A1* | 11/2018 | Abbasi ............... | A61B 17/7034 |
| 2022/0061891 A1* | 3/2022 | Lengyel ............. | A61B 17/7041 |

* cited by examiner

150

100

110

222

220

200

300

224

120

226

230 210

212

400

400

400

410

700

ORTHOPEDIC SCREW EXTENSION

The disclosure claims priority on U.S. Provisional Application Ser. No. 63/300,318 filed Jan. 18, 2022, which is incorporated herein by reference.

The disclosure is also a continuation-in-part of U.S. application Ser. No. 29/855,227 filed Sep. 30, 2022, which is incorporated herein by reference.

The disclosure relates generally to medical devices and medical device applications, more particularly to orthopedic devices, and still more particularly to an orthopedic screw extension for use in spinal implant applications.

BACKGROUND

When implanting screws and rods in the spine, there exists a need to extend the height of the tulip intraoperatively. The reasons for performing this maneuver include, but are not limited to, the bone holding the screw is too weak to reduce (pull the screw/bone up to the rod). One skilled in the art would appreciate the ability to adjust the height of the tulip in-situ. By adjusting the height, the implanted rod can be secured to each screw, thus distributing the biomechanical load to each screw and providing a stronger implanted system.

U.S. Pat. No. 8,663,289 discloses an extension that can be used for orthopedic applications. The threaded portion of the device in the '289 patent is incapable of threading into the screw it is extending without having to rotate the extension on the top of the screw.

In view of the current state of the art of spinal implants, there is a need for an improved device that can be used to adjust the height of the screw being used to connect to a rod.

SUMMARY OF THE DISCLOSURE

The present disclosure is direct to a medical device in the form of an orthopedic screw extension for use in spinal implant applications. The present invention is an improvement over existing orthopedic extensions in that the orthopedic extension can capture a locking screw independent of the height adjuster. This novel feature allows the tulip extension assembly to lock to the screw.

In accordance with a non-limiting aspect of the present disclosure, there is provided a medical device for use in spinal implant applications (e.g., orthopedic screw extension) that includes a body having a top portion and a bottom portion. The body generally has a circular cross-sectional shape; however, other cross-sectional shapes can be used (e.g., oval, triangular, square, rectangular, polygonal, etc.). In one non-limiting embodiment, the orthopedic screw extension is configured for use with a pedicle screw to facilitate in the connection to a spinal rod. The orthopedic screw extension can be used with fixed head pedicle screws. The orthopedic screw extension can threaded to or otherwise connected to the pedicle screw. As can be appreciated, although the orthopedic screw extension will be described with particular reference to pedicle screws, it will be appreciated that the orthopedic screw extension in accordance with the present disclosure can be used with other types of screws.

In accordance with another and/or alternative non-limiting aspect of the present disclosure, there is provided a medical device wherein the top portion of the body includes a top cavity. The internal surface of the top cavity can include a connection surface such as, but not limited to, a threaded surface. The cross-sectional shape of the top cavity is generally circular; however, other shapes can be used. The longitudinal length of the top cavity is generally 50-100% (and all values and ranges therebetween) of the longitudinal length of the top portion. In one non-limiting embodiment, the top cavity includes a connection arrangement in the form of a threaded connection arrangement. The top cavity includes a top opening that is configured to allow an instrument (e.g., screwdriver, locking tool, etc.) to be inserted into the top cavity of the top portion of the body to enable the instrument to access a device (e.g., locking screw, locking device, connecting screw, connecting device, etc.) and manipulate (e.g., turn, push, move, etc.) the device located in the top portion and/or bottom portion of the body of the orthopedic screw extension.

In accordance with another and/or alternative non-limiting aspect of the present disclosure, there is provided a medical device wherein the side of the top portion includes first and second top side openings that are configured to receive an orthopedic device (e.g., rod, etc.). The first and second top side openings are configured to be positioned on opposite sides of the top cavity and extend upwardly to the top opening of the top cavity of the top portion. The first and second top side openings form two or more upwardly extending arms in the top portion. The longitudinal length of the first and second top side openings generally extends 10-100% (and all values and ranges therebetween) of the longitudinal length of the top portion. In one non-limiting arrangement, after a rod is inserted through and/or into the first and second top side openings, a locking device can be inserted into the top opening in the top cavity and connected thereto (e.g., the locking screw can be threaded on the threaded surface in the cavity of the top portion, etc.) to secure and lock the rod in position relative to the body of the orthopedic screw extension. As can be appreciated, many different arrangement can be used to secure the orthopedic device (e.g., rod, etc.) to the top portion of the body of the orthopedic screw extension. In another non-limiting embodiment, the first and second openings have a generally U-shaped configuration; however; other shapes can be used (e.g., triangular, square, rectangular, polygonal, oval, etc.). Generally, the combined volume of the first and second top side openings constitute no more than 50% of the outer peripheral perimeter region of the top portion, and typically 5-45% (and all values and ranges therebetween) of the outer peripheral perimeter region of the top portion of the body. The size and shape of the first and second top side openings is generally the same; however, this is not required.

In accordance with another and/or alternative non-limiting aspect of the present disclosure, there is provided a medical device wherein the side of the top portion of the body can optionally include one or more slots and/or grooves that run partially or fully along the longitudinal length of the top portion of the body. The one or more slots and/or grooves generally do not penetrate fully through the side wall of the top portion. The size and shape of the one or more slots and/or grooves is non-limiting. The one or more slots and/or grooves (when used) can allow for 1) reduced material in the body, 2) reduced weight of the body, and/or 3) slight flexure of the body during insertion of a rod in the body and/or when locking the rod to the top portion. In one non-limiting embodiment, two slots and/or grooves are positioned in the top portion of the body and located generally normal (e.g., 70-120° and all values and ranges therebetween) to the first and second opening in the top portion of the body. Generally, the outer perimeter area of the one or more slots and/or grooves constitutes no more than 60% of the total outer peripheral area of the top portion, and typically 5-40% (and all values and ranges therebetween) of the total outer peripheral area of the top portion of the body.

In accordance with another and/or alternative non-limiting aspect of the present disclosure, there is provided a medical device wherein the bottom portion of the body generally has a longitudinal length that is 30-70% (and all values and ranges therebetween) of the longitudinal length of the top portion of the body and, typically, the bottom portion of the body generally has a longitudinal length that is 45-55% of the longitudinal length of the top portion of the body.

In accordance with another and/or alternative non-limiting aspect of the present disclosure, there is provided a medical device wherein there is provided a mid-opening that is positioned fully in the top portion, fully in the bottom portion, or partially in the top and bottom portion of the body of the orthopedic screw extension. The mid-opening is generally positioned about the central axis of the body of the orthopedic screw extension. The cross-sectional shape of the mid-opening is generally circular; however, this is not required. Generally, the longitudinal length of the mid-opening as measured along the longitudinal axis of the body is generally 5-40% (and all values and ranges therebetween) of the longitudinal length of the body. The maximum diameter of the mid-opening or the maximum cross-sectional area of the mid-opening is generally 50-90% (and all values and ranges therebetween) of the maximum diameter of the body or the maximum cross-sectional area of the body that contains the mid-opening. In one non-limiting embodiment, the mid-opening is absent one or more side openings.

In accordance with another and/or alternative non-limiting aspect of the present disclosure, there is provided a medical device wherein the bottom portion of the body includes a bottom cavity that is located below the mid-opening of the body. The size and/or shape of the bottom cavity of the bottom portion can be the same or different from the top cavity in the top portion. In one non-limiting embodiment, the cross-sectional shape of the bottom cavity is generally circular; however, other shapes can be used. The longitudinal length of the bottom cavity is generally 50-100% (and all values and ranges therebetween) of the longitudinal length of the bottom portion. The internal surface of the bottom cavity can optionally include a connection surface (e.g., threaded surface, etc.). The longitudinal length of the bottom cavity is generally 50-100% (and all values and ranges therebetween) of the longitudinal length of the bottom portion.

In accordance with another and/or alternative non-limiting aspect of the present disclosure, there is provided a medical device wherein the side of the bottom portion includes first and second bottom side openings that are configured to receive a) a portion of the head portion of a pedicle screw, or b) a portion of a top portion of another orthopedic screw extension. The first and second side opens of the bottom portion are configured to be positioned on opposite sides of the bottom cavity and extend downwardly to the bottom opening of the bottom cavity of the bottom portion. The first and second bottom side openings in the bottom portion form two or more downwardly extending arms in the bottom portion. The longitudinal length of the first and second bottom side openings generally extends 10-100% (and all values and ranges therebetween) of the longitudinal length of the bottom portion. In another non-limiting embodiment, the first and second bottom side openings in the bottom portion have a generally U-shaped configuration; however; other shapes can be used (e.g., triangular, square, rectangular, polygonal, oval, etc.). Generally, the combined volume of the first and second bottom side openings in the bottom portion constitute no more than 80% of the outer peripheral perimeter region of the bottom portion, and typically 30-75% (and all values and ranges therebetween) of the outer peripheral perimeter region of the bottom portion of the body. The size and shape of the first and second bottom side openings of the bottom portion are generally the same; however, this is not required. In one non-limiting embodiment, less than 50% (e.g., 0-49.00% and all values and ranges therebetween) of the first bottom side opening in the bottom portion is located directly beneath either the first or second top side openings in the top portion. Likewise, less than 50% (e.g., 0-49.00% and all values and ranges therebetween) of the second bottom side opening in the bottom portion is located directly beneath either the first or second side top openings in the top portion. In another non-limiting embodiment, the central longitudinal axis of the first bottom side opening in the bottom portion is about 25-90° (and all values and ranges therebetween) off-center from the central longitudinal axis of the first top side opening and/or second top side opening of the top portion. In another non-limiting embodiment, the central longitudinal axis of the second bottom side opening in the bottom portion is about 25-90° (and all values and ranges therebetween) off-center from the central longitudinal axis of the first top side opening and/or second top side opening of the top portion. In another non-limiting embodiment, the maximum width of the first bottom side opening of the bottom portion is optionally greater (5-50% greater and all values and ranges therebetween) than the maximum width of either of the first and second top side openings of the top portion. In another non-limiting embodiment, the maximum width of the second bottom side opening of the bottom portion is optionally greater (5-50% greater and all values and ranges therebetween) than the maximum width of either of the first or second top side openings of the top portion. In one non-limiting embodiment, the size and width of the first and second bottom side openings of the bottom portion are configured to receive a portion or all of the top of a pedicle screw and to inhibit or prevent the top of a pedicle screw from rotating relative to the bottom portion of the body of the orthopedic screw extension once the top of the pedicle screw is connected to the bottom portion of the body of the orthopedic screw extension. The slots in the bottom portion can be used to 1) reduce material in the body, 2) reduce weight of the body, and/or 3) allow for slight flexure of the body during connection of the bottom portion of the body to another device. In one non-limiting embodiment, two slots in the bottom portion of the body can be positioned normal (e.g., 70-120° and all values and ranges therebetween) to the slots in the top portion of the body. In another non-limiting embodiment, the one or more slots have a generally U-shaped configuration; however; other shapes can be used (e.g., V-shaped, top half of an H-shape, etc.). Generally, the outer perimeter area of the slots in the bottom portion constitutes no more than 80% of the total outer peripheral area of the bottom portion, and typically 5-70% (and all values and ranges therebetween) of the total outer peripheral area of the bottom portion of the body.

In accordance with another and/or alternative non-limiting aspect of the present disclosure, there is provided a medical device wherein the bottom portion includes one or more retention flanges on the interior surface of the bottom cavity and are located at and/or near the bottom end of the bottom cavity. The one or more bottom retention flanges are configured to maintain a connecting member within the bottom cavity. The top region of the bottom portion can optionally include one or more top retention flanges that are also configured to maintain the connecting member within the bottom cavity. In another non-limiting embodiment, one or more or all of the one or more top retention flanges are configured to not fully span across the bottom cavity of the bottom portion. In another non-limiting embodiment, one or more or all of the one or more bottom retention flanges are configured to not fully span across the bottom cavity of the bottom portion. In one non-limiting embodiment, the connecting member is configured to be rotatable within the bottom cavity (e.g., rotatable about a central axis of the bottom cavity, etc.). The connecting member can optionally include outer threading configured to engage a threaded portion in the top portion of a pedicle screw to thereby secure the pedicle screw to the bottom portion of the body of the orthopedic screw extension. In one non-limiting embodiment, the connecting member is configured to maintain its position along the longitudinal axis of the body in the bottom portion (e.g., move 0-5% and all values and ranges therebetween of the longitudinal length of the body) when the connecting member is rotated. The top portion of the connecting member generally includes a non-circular-shaped recess or extended member that can be engaged with a tool to rotate the connecting member. The connecting member can optionally include a central passageway through the connecting member that is configured to enable a tool to be inserted through the central passageway and allow a user to engage a structure on the pedicle screw and rotate the pedicle screw while the orthopedic screw extension is positioned on and/or connected to the top portion of the pedicle screw. The cross-sectional shape of the central passageway is non-limiting (e.g., circular, etc.).

In accordance with another and/or alternative non-limiting aspect of the present disclosure, there is provided a medical device wherein the bottom region of the bottom portion is shaped to fit in the shape of the top portion of the pedicle screw that is designed to receive a rod. The top portion of the pedicle screw generally includes two slots and a curved slot bottom having a shape and size that is similar to the profile of the rod when resting in the slots. The width of the slots in the top portion of the pedicle screw are generally slightly larger than the diameter of the rod so the rod can be slid downwardly in the slots and the bottom curved portion of the rod rests in the closely matched curved profile of the bottom of the slots. The inner surface of the bottom portion of the body of the orthopedic screw extension can optionally be shaped and sized to slide in the slots in the top portion of the pedicle screw and the bottom of the body of the orthopedic screw extension has a curved shape such that the bottom curved portion of the bottom portion rests in the curved profile of the bottom of the slots in the top portion of the pedicle screw. The bottom portion of the body of the orthopedic screw extension can optionally include side extensions that are configured to overlie a portion of the sides of the outer surface of the top portion of the pedicle screw that are positioned adjacent to the slots in the top portion of the pedicle screw (e.g., extend a distance of 0.001-0.5 inches and all values and ranges therebetween from the side of the slot). The side extensions can be positioned on one or both sides of one or both slots in the top portion of the pedicle screw when the orthopedic screw extension is connected to the pedicle screw. The side extensions can extend partially or fully along the longitudinal length of one or both slots in the top portion of the pedicle screw when the orthopedic screw extension is connected to the pedicle screw (e.g., extend 5-100% and all values and ranges therebetween the longitudinal length of the slot in the top portion of the pedicle screw). The inner surface shape and/or the side extensions on the bottom portion can be used to facilitate in a) the proper positioning of the orthopedic screw extension on the top portion of the pedicle screw, b) reduce movement of the orthopedic screw extension relative to the top portion of the pedicle screw when the orthopedic screw extension is connected to the pedicle screw, c) form an improved rigid connection between the orthopedic screw extension and the top portion of the pedicle screw when the orthopedic screw extension is connected to the pedicle screw, and/or d) form a stronger connection between the orthopedic screw extension and the top portion of the pedicle screw when the orthopedic screw extension is connected to the pedicle screw.

In one non-limiting arrangement, after a rod is inserted through and/or into the first and second top side openings, a locking device can be inserted into the top opening in the top cavity and connected thereto (e.g., the locking screw can be threaded on the threaded surface in the cavity of the top portion, etc.) to secure and lock the rod in position relative to the body of the orthopedic screw extension. As can be appreciated, many different arrangement can be used to secure the orthopedic device (e.g., rod, etc.) to the top portion of the body of the orthopedic screw extension. In another non-limiting embodiment, the first and second openings have a generally U-shaped configuration; however; other shapes can be used (e.g., triangular, square, rectangular, polygonal, oval, etc.).

The bottom portion of the orthopedic screw extension in accordance with the present disclosure can be configured to enable the orthopedic screw extension to be adjustable in height when connected to the top of an orthopedic screw or post. Such a feature is advantageous in that the orthopedic screw extension can be adjusted to the desired height for a particular application, thereby reducing stress on the bone and/or orthopedic structures when attached to the bone of a patient.

In accordance with another and/or alternative non-limiting aspect of the present disclosure, there is provided a medical device such as, but not limited to, an orthopedic screw extension for use in spinal implant applications (e.g., orthopedic screw tulip extension) that can be formed of a variety of materials such as, but not limited to, stainless steel, cobalt chromium alloy, TiAl alloy, rhenium-containing alloy (e.g., a metal alloy having a rhenium content of 2-19.99 wt. % and all values and ranges therebetween), or a refractory metal alloy. As defined herein, a refractory metal alloy is a metal alloy that includes at least 20 wt. % of one or more of molybdenum, rhenium, niobium, tantalum, or tungsten. Non-limiting refractory metal alloys include MoRe alloy, ReW alloy, MoReCr alloy, MoReTa alloy, MoReTi alloy, WCu alloy, molybdenum alloy, rhenium alloy, tungsten alloy, tantalum alloy, niobium alloy, etc. In one non-limiting embodiment, 90-100% of the body of the medical device is formed of a MoRe alloy. In another non-limiting embodiment, at least 30 wt. % (e.g., 30-100 wt. % and all values and ranges therebetween) of the refractory metal alloy includes one or more of molybdenum, rhenium, niobium, tantalum, or tungsten. In another non-limiting embodiment, at least 50 wt. % of the refractory metal alloy includes one or more of molybdenum, rhenium, niobium, tantalum, or tungsten. In another non-limiting embodiment, at least 50 wt. % (e.g., 50-100 wt. % and all values and ranges therebetween) of the refractory metal alloy includes one or more of molybdenum, rhenium, niobium, tantalum, or tungsten, and 0-40 wt. % (and all values and ranges therebetween) of the refractory alloy includes one or more of titanium, vanadium, chromium, manganese, zirconia, technetium, ruthenium, rhodium, hafnium, osmium, copper, or iridium. In another non-limiting embodiment, at least 50 wt. % (e.g., 50-99.9 wt. % and all values and ranges therebetween) of the refractory metal alloy includes one or more of molybdenum, rhenium, niobium, tantalum, or tungsten, and 0.1-40 wt. % (and all values and ranges therebetween) of the refractory alloy includes one or more of titanium, vanadium, chromium, manganese, zirconia, technetium, ruthenium, rhodium, hafnium, osmium, copper, or iridium. In another non-limiting embodiment, at least 50 wt. % (e.g., 50-100 wt. % and all values and ranges therebetween) of the refractory metal alloy includes one or more of molybdenum, rhenium, niobium, tantalum, or tungsten, and 0-40 wt. % (and all values and ranges therebetween) of the refractory alloy includes one or more of titanium, vanadium, chromium, manganese, zirconia, technetium, ruthenium, rhodium, hafnium, osmium, copper, or iridium, and the refractory alloy includes 0-2 wt. % (and all values and ranges therebetween) of a combination of other metals, carbon, oxygen, and nitrogen. In another non-limiting embodiment, at least 50 wt. % (e.g., 50-99.9 wt. % and all values and ranges therebetween) of the refractory metal alloy includes one or more of molybdenum, rhenium, niobium, tantalum, or tungsten, and 0.1-40 wt. % (and all values and ranges therebetween) of the refractory alloy includes one or more of titanium, vanadium, chromium, manganese, zirconia, technetium, ruthenium, rhodium, hafnium, osmium, copper, or iridium, and the refractory alloy includes 0-2 wt. % (and all values and ranges therebetween) of a combination of other metals, carbon, oxygen, and nitrogen. In another non-limiting embodiment, at least 55 wt. % of the refractory metal alloy includes one or more of molybdenum, rhenium, niobium, tantalum, or tungsten, and 0-40 wt. % of the refractory alloy includes one or more of titanium, vanadium, chromium, manganese, zirconia, technetium, ruthenium, rhodium, hafnium, osmium, copper, or iridium, and the refractory alloy includes 0-0.1 wt. % of a combination of other metals, carbon, oxygen, and nitrogen. In another non-limiting embodiment, at least 55 wt % of the refractory metal alloy includes one or more of molybdenum, rhenium, niobium, tantalum, or tungsten, and 0.1-40 wt. % of the refractory alloy includes one or more of titanium, vanadium, chromium, manganese, zirconia, technetium, ruthenium, rhodium, hafnium, osmium, copper, or iridium, and the refractory alloy includes 0-0.1 wt. % of a combination of other metals, carbon, oxygen, and nitrogen. When the medical device is partially or fully formed of a refractory metal alloy, the refractory metal alloy can be used to 1) increase the radiopacity of the medical device, 2) increase the radial strength of the medical device, 3) increase the yield strength and/or ultimate tensile strength of the medical device, 4) improve the stress-strain properties of the medical device, 5) improve the strength and/or durability of the medical device, 6) increase the hardness of the medical device, 7) improve the biostability and/or biocompatibility properties of the medical device, 8) resist cracking in the medical device and resist propagation of cracks, 9) increase yield strength of the medical device, 10) improve durability of the medical device, 11) reduce adverse tissue reactions after implant of the medical device, 12) reduce metal ion release after implant of the medical device, 13) reduce corrosion of the medical device, 14) reduce allergic reaction after implant of the medical device, 15) improve hydrophilicity of the medical device, and/or 16) reduce toxicity of the medical device after implant of the medical device. The medical device generally includes one or more materials that impart the desired properties to the medical device to withstand the manufacturing processes needed to produce the medical device. These manufacturing processes can include, but are not limited to, laser cutting, etching, annealing, drawing, pilgering, electroplating, electro-polishing, machining, plasma coating, 3D printed coatings, 3D printing, chemical vapor deposition, chemical polishing, cleaning, pickling, ion beam deposition or implantation, sputter coating, vacuum deposition, etc. In one non-limiting embodiment, the medical device is at least partially or fully formed by a 3D printing process.

In another and/or alternative non-limiting aspect of the present disclosure, the metal alloy used to partially or fully form the medical device can be nitrided; however, this is not required. The thickness of the nitrided surface layer is less than about 1 mm. In one non-limiting embodiment, the thickness of the nitrided surface layer is at least about 50 nm and less than about 1 mm (and all values and ranges therebetween). In another non-limiting embodiment, the thickness of the nitrided surface layer is at least about 50 nm and less than about 0.1 mm. When a MoRe alloy is nitrided, the weight percent of the nitrogen in the nitrided surface layer is less than a weight percent of the molybdenum in the nitrided surface layer. Also, the weight percent of nitrogen in the nitrided surface layer is less than a weight percent of the rhenium in the nitrided surface layer. In one non-limiting composition of the nitrided surface layer on a MoRe alloy (e.g., 40-99 wt. % molybdenum, 1-40 wt. % rhenium), the nitride surface layer comprises 40-99 wt. % molybdenum (and all values and ranges therebetween), 1-40 wt. % rhenium (and all values and ranges therebetween), and 0.0001-5 wt. % nitrogen (and all values and ranges therebetween). In another non-limiting composition of the nitrided surface layer, the nitrided surface layer comprises 40-99 wt. % molybdenum, 1-40 wt. % rhenium, and 0.001-1 wt. % nitrogen. The nitriding process can be used to increase surface hardness and/or wear resistance of the medical device, and/or inhibits or prevents discoloration of the refractory metal alloy (e.g., discoloration by oxidation, etc.). For example, the nitriding process increases the wear resistance of articulation surfaces or surfaces wear on the refractory metal alloy used in the medical device to extend the life of the medical device, increases the wear life of mating surfaces on the medical device, and/or reduces particulate generation from use of the medical device, and/or maintains the outer surface appearance of the metal alloy on the medical device.

In yet another and/or alternative non-limiting aspect of the present disclosure, the medical device can include, contain, and/or be coated with one or more agents that facilitate in the success of the medical device and/or treated area. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. The type and/or amount of an agent included in a medical device and/or coated on medical device can vary. When two or more agents are included in and/or coated on medical device, the amount of two or more agents can be the same or different. The type and/or amount of agent included on, in and/or in conjunction with medical device are generally selected to address one or more clinical events. Typically, the amount of agent included on, in, and/or used in conjunction with the medical device is about 0.01-100 ug per mm$^2$ and/or at least about 0.00001 wt. % of the device; however, other amounts can be used. In one non-limiting embodiment of the disclosure, the medical device can be partially or fully coated and/or impregnated with one or more agents to facilitate in the success of a particular medical procedure.

In a further and/or alternative non-limiting aspect of the present disclosure, the one or more agents on and/or in the medical device (when used) can be released in a controlled manner to provide the area in question to be treated with the desired dosage of agent over a sustained period of time. The medical device can be designed such that 1) all the agent on and/or in the medical device is controllably released, 2) some of the agent on and/or in the medical device is controllably released and some of the agent on the medical device is non-controllably released, or 3) none of the agent on and/or in the medical device is controllably released. The medical device can also be designed such that the rate of release of the one or more agents from the medical device is the same or different. The medical device can also be designed such that the rate of release of the one or more agents from one or more regions on the medical device is the same or different. Non-limiting arrangements that can be used to control the release of one or more agents from the medical device include 1) at least partially coating one or more agents with one or more polymers, 2) at least partially incorporating and/or at least partially encapsulating one or more agents into and/or with one or more polymers, and/or 3) inserting one or more agents in pores, passageway, cavities, etc., in the medical device and at least partially coating or covering such pores, passageway, cavities, etc., with one or more polymers. As can be appreciated, other or additional arrangements can be used to control the release of one or more agents from the medical device. The thickness of each polymer layer and/or layer of agent is generally at least about 0.01 μm and is generally less than about 150 μm (e.g., 0.01-149.9999 μm and all values and ranges therebetween). In one non-limiting embodiment, the thickness of a polymer layer and/or layer of agent is about 0.02-75 μm, more particularly about 0.05-50 μm, and even more particularly about 1-30 μm.

In yet another and/or alternative non-limiting aspect of the disclosure, the medical device can include a marker material. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.), and/or other types of electromagnetic waves (e.g., microwaves, visible light, infrared waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion, at ends of medical device, at or near transition of body portion and flaring section, etc.) of the medical device. The location of the marker material can be on one or multiple locations on the medical device. The size of the one or more regions that include the marker material can be the same or different.

In a further and/or alternative non-limiting aspect of the present disclosure, the medical device or one or more regions of the medical device can be constructed by use of one or more microelectromechanical manufacturing (MEMS) techniques (e.g., micro-machining, laser micro-machining, laser micro-machining, micro-molding, etc.); however, other or additional manufacturing techniques can be used.

In still yet another and/or alternative non-limiting aspect of the present disclosure, there is provided a near net process for a body or other metal component of the medical device. In one non-limiting embodiment of the disclosure, there is provided a method of powder pressing materials and increasing the strength post sintering by imparting additional cold work. In one non-limiting embodiment, the green part is pressed and then sintered. Thereafter, the sintered part is again pressed to increase its mechanical strength by imparting cold work into the pressed and sintered part. Generally, the temperature during the pressing process after the sintering process is 20-100° C. (and all values and ranges therebetween), typically 20-80° C., and more typically 20-40° C. As defined herein, cold working occurs at a temperature of no more than 150° C. (e.g., 10-150° C. and all values and ranges therebetween). The change in the shape of the repressed post-sintered part needs to be determined so the final part (pressed, sintered and re-pressed) meets the dimensional requirements of the final formed part. For a Mo47.5Re alloy, MoRe alloy, ReW alloy, molybdenum alloy, tungsten alloy, rhenium alloy, other type of refractory metal alloy, or TWIP alloy formed of a high titanium content, a prepress pressure of 1-300 tsi (1 ton per square inch) (and all values and ranges therebetween) can be used followed by a sintering process of at least 1600° C. (e.g., 1600-2600° C. and all values and ranges therebetween) and a post sintering press at a pressure of 1-300 tsi (and all values and ranges therebetween) at a temperature of at least 20° C. (e.g., 20-100° C. and all values and ranges therebetween; 20-40° C., etc.). There is also provided a process of increasing the mechanical strength of a pressed metal part by repressing the post-sintered part to add additional cold work into the material, thereby increasing its mechanical strength. There is also provided a process of powder pressing to a near net or final part using metal powder. In one non-limiting embodiment, the metal powder used to form the near net or final part includes a minimum of 40% rhenium by weight and at least 30% molybdenum, and the remainder can optionally include one or more elements of tungsten, tantalum, zirconium, iridium, titanium, bismuth, and yttrium. In another non-limiting embodiment, the metal powder used to form the near net or final part includes 20-80 wt. % rhenium (and all values and ranges therebetween), 20-80 wt. % molybdenum (and all values and ranges therebetween), and optionally one or more elements of tungsten, tantalum, zirconium, iridium, titanium, bismuth, and yttrium. In another non-limiting embodiment, the metal powder used to form the near net or final part includes tungsten (20-60 wt. % and all values and ranges therebetween), rhenium (20-80 wt. % and all values and ranges therebetween) and one or more other elements 0-5 wt. % (and all values and ranges therebetween). In another non-limiting embodiment, the metal powder used to form the near net or final part includes tungsten (20-80 wt. % and all values and ranges therebetween), rhenium (20-80 wt. % and all values and ranges therebetween), molybdenum (0-15 wt. % and all values and ranges therebetween), and one or more other elements 0-5 wt. % (and all values and ranges therebetween). In another non-limiting embodiment, the metal powder used to form the near net or final part includes tungsten (20-80 wt. % and all values and ranges therebetween), copper (1-30 wt. % and all values and ranges therebetween), and one or more other elements 0-5 wt. % (and all values and ranges therebetween). In another non-limiting embodiment, the metal powder used to form the near net or final part includes a titanium alloy or a cobalt alloy. The ductility of the refractory metal alloy measured as % reduction in area can increase the yield and ultimate tensile strength can increase.

In still yet another and/or alternative non-limiting aspect of the present disclosure, there is provided a press of near net or finished part composite. The process of pressing metals into near net or finished parts is well established; however, pressing a composite structure formed of metal powder and polymer for purposes of making complex part geometries and foam-like structures is new. Similarly, using a pressing process to impart particular biologic substances into the metal matrix is also new. In one non-limiting embodiment, there is provided a process of creating a metal part with pre-defined voids to create a trabecular or foam structure composed of mixing a metal and polymer powder, pressing the powder into a finished part or semi-finished green part, and then sintering the part under conditions in which the polymer leaves the metal behind through a process of thermal degradation of the polymer. The resulting part has a porosity associated with the size of the polymer particles as well as the homogeneity of the mixture upon pressing prior to sintering. In another non-limiting embodiment, there is provided a process by which a residual of the polymer is left behind after thermal degradation, on the metal substrate, and the polymer residual has some desired biological affect (e.g., masking the metal from the body by encapsulation, promotion of cellular attachment and growth). The polymer and metal powders can be of varying sizes to create multiple voids—some large, creating a pathway for cellular growth, and some small, creating a ruff surface to promote cellular attachment.

As can be appreciated, the polymer can be uniformly or non-uniformly dispersed with the metal powder. For example, if the final formed part is to have a uniform density and pore structure, the polymer material is uniformly dispersed with the metal powder prior to consolidating and pressing the polymer and metal powders together and then subsequently sintering together the metal powder to form the metal part or medical device. Alternatively, if the formed metal part or medical device is to have one or more channels, passageways, and/or voids on the outer surface and/or within the formed part or medical device, at least a portion of the polymer is not uniformly distributed with the metal powder, but instead is concentrated or forms all of the region that is to be the one or more channels, passageways, and/or voids on the outer surface and/or within the formed part or medical device such that when the polymer and metal powder is sintered, some or all of the polymer is degraded and removed from the part or medical device thereby forming such one or more channels, passageways, and/or voids on the outer surface and/or within the formed part or medical device. As such, the use of polymer in combination with metal powder and subsequent pressing and sintering can be used to form novel and customized shapes for medical device or the near net form of the medical device. Generally, the polymer constitutes about 0.1-70 vol. % (and all values and ranges therebetween) of the consolidated and pressed material prior to the sintering step, typically the polymer constitutes about 1-60 vol. % of the consolidated and pressed material prior to the sintering step, more typically the polymer constitutes about 2-50 vol. % of the consolidated and pressed material prior to the sintering step, and even more typically the polymer constitutes about 2-45 vol. % of the consolidated and pressed material prior to the sintering step. As such, if the polymer constitutes about 5 vol. % of the consolidated and pressed material prior to the sintering step, and after the sintering step at least 99% of the polymer is degraded and removed from the part or medical device, then the part could include up to about 5 vol. % cavities and/or passageways in the part or medical device.

The types of polymer and metal powder are non-limiting. The polymer and metal powders can be of varying sizes to create multiple voids/passageways/channels which can be used to create a pathway for cellular growth, create a ruff surface to promote cellular attachment, have a biological agent inserted into one or more of the voids/passageways/channels, have biological material inserted into one or more of the voids/passageways/channels, etc. In one non-limiting embodiment, the average particle size of the polymer is greater than the average particle size of the metal powder.

In another non-limiting aspect of the present disclosure, after the sintering process, at least 98 vol. % of the polymer is thermally degraded and/or removed from the sintered material, typically at least 99 vol. % of the polymer is thermally degraded and/or removed from the sintered material, more typically at least 99.5 vol. % of the polymer is thermally degraded and/or removed from the sintered material, still even more typically at least 99.9 vol. % of the polymer is thermally degraded and/or removed from the sintered material, and even still more typically at least 99.95 vol. % of the polymer is thermally degraded and/or removed from the sintered material. The resulting part or medical device has a porosity associated with the size of the polymer particles as well as the homogeneity of the mixture upon pressing prior to sintering.

In another non-limiting aspect of the present disclosure, after the sintering process, some of the polymer remains in the sintered part or the medical device. The remaining polymer in the sintered part or the medical device can optionally have some desired biological affect (e.g., masking the metal from the body by encapsulation, promoting cellular attachment and growth). The remaining polymer can optionally include one or more biological agents that remain active after the sintering process. In one non-limiting embodiment, after the sintering process, about 5-97.5 vol. % (and all values and ranges therebetween) of the polymer is thermally degraded and/or removed from the sintered material, typically about 10-95 vol. % of the polymer is thermally degraded and removed from the sintered material, and more typically about 10-80 vol. % of the polymer is thermally degraded and removed from the sintered material.

In a further and/or alternative non-limiting aspect of the present disclosure, the refractory metal alloy used to at least partially form the medical device is initially formed into a blank, a rod, a tube, etc., and then finished into final form by one or more finishing processes. The refractory metal alloy blank, rod, tube, etc., can be formed by various techniques such as, but not limited to, 1) melting the refractory metal alloy and/or metals that form the refractory metal alloy (e.g., vacuum arc melting, etc.) and then extruding and/or casting the refractory metal alloy into a blank, rod, tube, etc., 2) melting the refractory metal alloy and/or metals that form the refractory metal alloy, forming a metal strip and then rolling and welding the strip into a blank, rod, tube, etc., or 3) consolidating metal power of the refractory metal alloy and/or metal powder of metals that form the refractory metal alloy into a blank, rod, tube, etc. When the refractory metal alloy is formed into a blank, the shape and size of the blank is non-limiting. In one non-limiting process, the near net medical device, blank, rod, tube, etc., can be formed from one or more ingots of metal or refractory metal alloy. In one non-limiting process, an arc melting process (e.g., vacuum arc melting process, etc.) can be used to form the near net medical device, blank, rod, tube, etc. In another non-limiting process, rhenium powder and tungsten powder and optionally molybdenum powder can be placed in a crucible (e.g., silica crucible, etc.) and heated under a controlled atmosphere (e.g., vacuum environment, carbon monoxide environment, hydrogen and argon environment, helium, argon, etc.) by an induction melting furnace to form the near net medical device, blank, rod, tube, etc. As can be appreciated, other metal particles can be used to form other refractory metal alloys (e.g., Mo alloys, Re alloys, MoReCr alloys, FeCrMoCB alloys, WCu alloys, WRe alloys, etc.) by various processes such as melting, sintering, particle compression plus heat, etc. It can be appreciated that other or additional processes can be used to form the refractory metal alloy. In still another and/or additional non-limiting process, the near net medical device, blank, rod, tube, etc., of the refractory metal alloy is formed by consolidating metal powder. In this process, fine particles of metal (e.g., rhenium, tungsten, molybdenum, titanium, copper, nickel, chromium, etc.) along with any additives are mixed to form a homogenous blend of particles. Typically, the average particle size of the metal powders is less than about 200 mesh (e.g., less than 74 microns). A larger average particle size can interfere with the proper mixing of the metal powders and/or adversely affect one or more physical properties of the near net medical device, blank, rod, tube, etc., formed from the metal powders. In one non-limiting embodiment, the average particle size of the metal powders is less than about 230 mesh (e.g., less than 63 microns). In another and/or alternative non-limiting embodiment, the average particle size of the metal powders is about 2-63 microns, and more particularly about 5-40 microns. As can be appreciated, smaller average particle sizes can be used. The purity of the metal powders should be selected so that the metal powders contain very low levels of carbon, oxygen, and nitrogen. Typically, the carbon content of the metal powder used to form the refractory metal alloy is less than about 100 ppm, the oxygen content is less than about 50 ppm, and the nitrogen content is less than about 20 ppm. Typically, metal powder used to form the refractory metal alloy has a purity grade of at least 99.9 and more typically at least about 99.95. The blend of metal powder is then pressed together to form a solid solution of the refractory metal alloy into a near net medical device, blank, rod, tube, etc. Typically, the pressing process is by an isostatic process (i.e., uniform pressure applied from all sides on the metal powder); however other processes can be used. When the metal powders are pressed together isostatically, cold isostatic pressing (CIP) is typically used to consolidate the metal powders; however, this is not required. The pressing process can be performed in an inert atmosphere, an oxygen-reducing atmosphere (e.g., hydrogen, argon and hydrogen mixture, etc.) and/or under a vacuum; however, this is not required. The average density of the near net medical device, blank, rod, tube, etc., that is achieved by pressing together the metal powders is about 80-95% (and all values and ranges therebetween) of the final average density of the near net medical device, blank, rod, tube, etc., or about 70-96% (and all values and ranges therebetween) the minimum theoretical density of the refractory metal alloy. Pressing pressures of at least about 300 MPa are generally used. Generally, the pressing pressure is about 400-700 MPa; however, other pressures can be used. After the metal powders are pressed together, the pressed metal powders are sintered at a temperature of at least 1600° C. (e.g., 1600-3500° C. and all values and ranges therebetween) to partially or fully fuse the metal powders together to form the near net medical device, blank, rod, tube, etc. The sintering of the consolidated metal powder can be performed in an oxygen-reducing atmosphere (e.g., helium, argon, hydrogen, argon and hydrogen mixture, etc.) and/or under a vacuum; however, this is not required. At the high sintering temperatures, a high hydrogen atmosphere will reduce both the amount of carbon and oxygen in the formed near net medical device, blank, rod, tube, etc. The sintered metal powder generally has an as-sintered average density of about 90-99% the minimum theoretical density of the refractory metal alloy. Typically, the sintered refractory metal alloy has a final average density of at least about 5 gm/cc, and typically at least about 8.3 gm/cc, and can be up to or greater than about 16 gm/cc; however, this is not required. The density of the formed near net medical device, blank, rod, tube, etc., will generally depend on the type of refractory metal alloy used.

In yet a further and/or alternative non-limiting aspect of the present disclosure, the near net medical device, blank, rod, tube, etc., can be cleaned and/or polished after the near net medical device, blank, rod, tube, etc., has been formed; however, this is not required. Typically, the near net medical device, blank, rod, tube, etc., is cleaned and/or polished prior to being further processed; however, this is not required.

In one non-limiting object of the present disclosure is the provision of an orthopedic screw extension configured to connect to an orthopedic screw and an orthopedic rod. The orthopedic screw extension comprises a body that has a top portion and a bottom portion. The top portion includes a top cavity. The bottom portion includes a bottom cavity. The top portion includes two top side openings that are configured to receive a portion of the orthopedic rod. The two top side openings form first and second upwardly extending arms. The top cavity includes a top securing surface configured to receive connector to entrap the orthopedic rod in the two top side openings. The bottom cavity includes two bottom side openings that are configured to receive a top portion of the orthopedic screw. The two bottom side openings form first and second downwardly extending arms. The body includes a connecting member that is located between top and bottom ends of the body. The connecting member is movable relative to the body. The connecting member is configured to connect to the top portion of the orthopedic screw.

In one non-limiting object of the present disclosure is the provision of an orthopedic screw extension configured to connect to an orthopedic screw and an orthopedic rod wherein the top securing surface includes a threaded surface.

In one non-limiting object of the present disclosure is the provision of an orthopedic screw extension configured to connect to an orthopedic screw and an orthopedic rod wherein the body includes a mid-opening that is positioned along a longitudinal axis of the body, and wherein the opening forms a passageway between the top and bottom cavities.

In one non-limiting object of the present disclosure is the provision of an orthopedic screw extension configured to connect to an orthopedic screw and an orthopedic rod wherein a) the first and second bottom side openings are positioned on opposite sides of the bottom cavity, and/or b) the first and second top side openings are positioned on opposite sides of the top cavity.

In one non-limiting object of the present disclosure is the provision of an orthopedic screw extension configured to connect to an orthopedic screw and an orthopedic rod wherein a) less than 50% of the first bottom side opening is located directly beneath either the first and second top side openings in the top portion, and/or b) less than 50% of the second bottom side opening is located directly beneath either the first and second top side openings.

In one non-limiting object of the present disclosure is the provision of an orthopedic screw extension configured to connect to an orthopedic screw and an orthopedic rod wherein a) a maximum width of the first bottom side opening of the bottom portion is greater than a maximum width of either of the first or second top side openings in the top portion, and/or b) a maximum width of the second bottom side opening of the bottom portion is greater than a maximum width of either of the first or second top side openings in the top portion.

In one non-limiting object of the present disclosure is the provision of an orthopedic screw extension configured to connect to an orthopedic screw and an orthopedic rod wherein a) the bottom portion includes one or more retention flanges on an inner surface of the bottom cavity, and/or b) said one or more retention flanges engages the connecting member to prevent the connection member to move out of a bottom of the bottom cavity.

In one non-limiting object of the present disclosure is the provision of an orthopedic screw extension configured to connect to an orthopedic screw and an orthopedic rod wherein the connecting member is rotatable within the body.

In one non-limiting object of the present disclosure is the provision of an orthopedic screw extension configured to connect to an orthopedic screw and an orthopedic rod wherein the connecting member includes an opening fully through the longitudinal axis of the connecting member.

In one non-limiting object of the present disclosure is the provision of an orthopedic screw extension configured to connect to an orthopedic screw and an orthopedic rod wherein a) an inner surface of the first and second downwardly extending arms include inwardly extending flanges that are configured to engage a side surface of a slot in a head portion of the pedicle screw when the orthopedic screw extension is connected to the pedicle screw, and/or b) the first and second downwardly extending arms include side extensions that are configured to overlie a portion of an outer surface of a head portion of the pedicle screw when the orthopedic screw extension is connected to the pedicle screw. In one non-limiting embodiment, the inwardly extending flanges are positioned normal to the inner surface of the downwardly extending arms.

In another non-limiting embodiment, the distance the inwardly extending flanges extend from the inner surface of the downwardly extending arms is less than a width of the side extensions measure from the side of the inwardly extending flange to the side edge of the downwardly extending arm.

In another non-limiting embodiment, an orthopedic screw assembly comprises a) an orthopedic screw having a threaded portion for implantation into a bone and a head portion that includes two side slots in the head portion that form two upwardly extending flanges; b) an orthopedic rod; c) an orthopedic screw extension configured to connect to said orthopedic screw and said orthopedic rod, wherein the orthopedic screw extension includes features are described above, and d) a locking screw configured to connect to the top portion of the body and to entrap the orthopedic rod in the two top side openings.

In another non-limiting embodiment, there is the embodiment of a method of treating a bone comprising a) providing an orthopedic screw; wherein the orthopedic screw includes a threaded portion for implantation into the bone and a head portion that includes two side slots in said head portion that form two upwardly extending flanges; b) providing an orthopedic rod; c) providing an orthopedic screw extension, wherein the orthopedic screw extension includes features are described above; d) connecting the threaded portion of the orthopedic screw to the bone; e) connecting the bottom portion of the body of the orthopedic screw extension to a portion of the head portion of the orthopedic screw; and f) connecting the orthopedic rod to the top portion of the body of the orthopedic screw extension.

These and other advantages will become apparent to those skilled in the art upon the reading and following of this description.

BRIEF DESCRIPTION OF THE DRAWINGS

Reference may now be made to the drawings, which illustrate various embodiments that the disclosure may take in physical form and in certain parts and arrangement of parts wherein.

DESCRIPTION OF NON-LIMITING EMBODIMENTS

Figure 1:
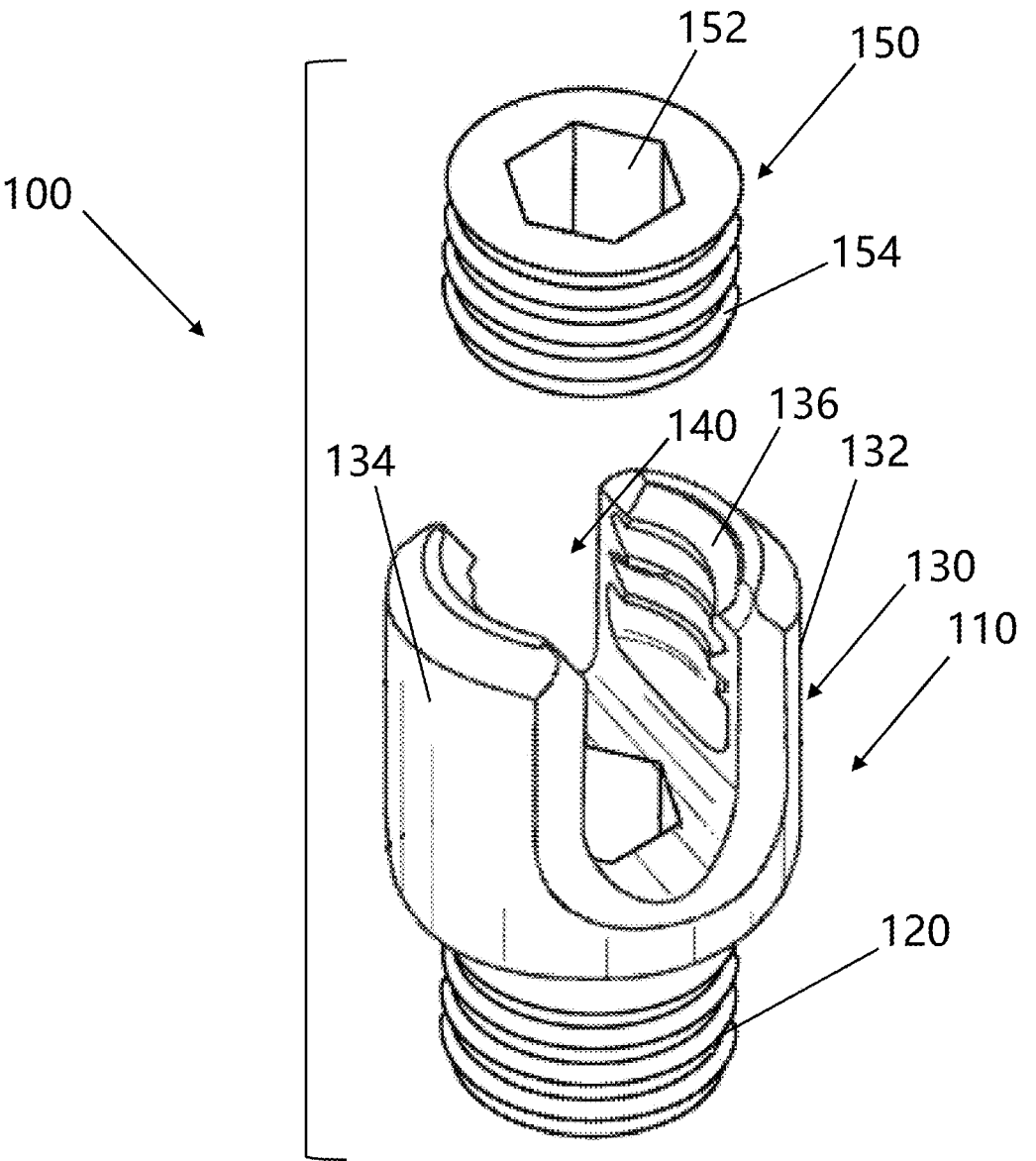
FIG. 1 is a perspective exploded view of a prior art pedicle screw head extender.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g. "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Figure 2:
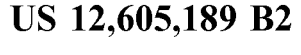
FIG. 2 is a perspective view of a pedicle screw with the prior art pedicle screw head extender illustrated in FIG. 1 positioned thereon with a spinal rod attached thereto.

FIGS. 1 and 2 illustrate a prior art pedicel screw extender 100 and the connection of prior art pedicel screw extender 100 to a prior art fixed head pedicle screw 200 as illustrated in U.S. Pat. No. 8,663,289, which is fully incorporated herein by reference.

The pedicle screw extender 100 includes a body 110 having a threaded portion 120 at the bottom portion of body 110. The upper portion 130 of body 110 includes two upwardly extending flanges 132, 134 that form a cavity 140 therebetween. Upwardly extending flanges 132, 134 include threads 136. Threads 136 are configured to threadedly secure a locking screw 150 to body 110. Locking screw 150 includes a cavity 152 that is configured to receive a tool used to insert or remove locking screw 150 from body 110. Locking screw 150 includes threads 154 that threadedly connect to threads 136 on upwardly extending flanges 132, 134. The bottom portion of the body 110 includes an opening 160 that is configured to receive a tool used to install the pedicle screw extender 100 onto a pedicle screw.

FIG. 2 illustrates pedicle screw extender 100 of FIG. 1 installed on a typical fixed head pedicle screw 200. Fixed head pedicle screw 200 has an elongated stem 210 that includes threads 212. Threads 212 are used to secure fixed head pedicle screw 200 to a bone (not shown). Fixed head pedicle screw 200 includes a cylindrical head 220 having a pair of upwardly extending flanges 222, 224 that form a cavity 226 therebetween. The inner surface of upwardly extending flanges 222, 224 includes threading that is configured to threadedly connect to threading 120 on body 110 of pedicle screw extender 100 to thereby secure pedicle screw extender 100 to fixed head pedicle screw 200. Fixed head pedicle screw 200 includes an opening 230 that is configured to receive a tool for the installation of fixed head pedicle screw 200 into a bone. An orthopedic rod 300 is connected to pedicle screw extender 100 by securing orthopedic rod 300 in cavity 140 by locking screw 150.

Referring now to FIGS. 3-8, there is illustrated a non-limiting orthopedic screw extension 400 in accordance the present disclosure, and the use of orthopedic screw extension 400 in accordance the present disclosure in a non-limiting application of securing orthopedic screw extension 400 to an orthopedic rod 300.

The orthopedic screw extension includes a body 410 having a top portion 420 and a bottom portion 430. Body 410 generally has a circular cross-sectional shape; however, other cross-sectional shapes can be used (e.g., oval, triangular, square, rectangular, polygonal, etc.).

Top portion 420 of body 410 includes a top cavity 500. The internal surface of top cavity 500 can include a connection surface such as, but not limited to, a threaded surface 510. The cross-sectional shape of top cavity 500 is generally circular; however, other shapes can be used. Top cavity 500 includes a top opening 520 that is configured to allow an instrument (e.g., screwdriver, locking tool, etc.) to be inserted into top cavity 500 of portion 420 to enable the instrument to access a device (e.g., locking screw, locking device, connecting screw, connecting device, etc.) and manipulate (e.g., turn, push, move, etc.) the connecting member 700 that is located in body 410 of orthopedic screw extension 400.

The side of top portion 420 includes first and second top side openings 440, 450 that are configured to receive an orthopedic rod 300. First and second side opens 440, 450 are configured to be positioned on opposite sides of the top cavity 500 and extend upwardly to the top opening of the top cavity of the top portion. First and second top side openings 440, 450 from two upwardly extending arms 460, 470 in top portion 420. The longitudinal length of first and second top side openings 440, 450 generally extends 50-100% of the longitudinal length of top portion 420.

Figure 8:
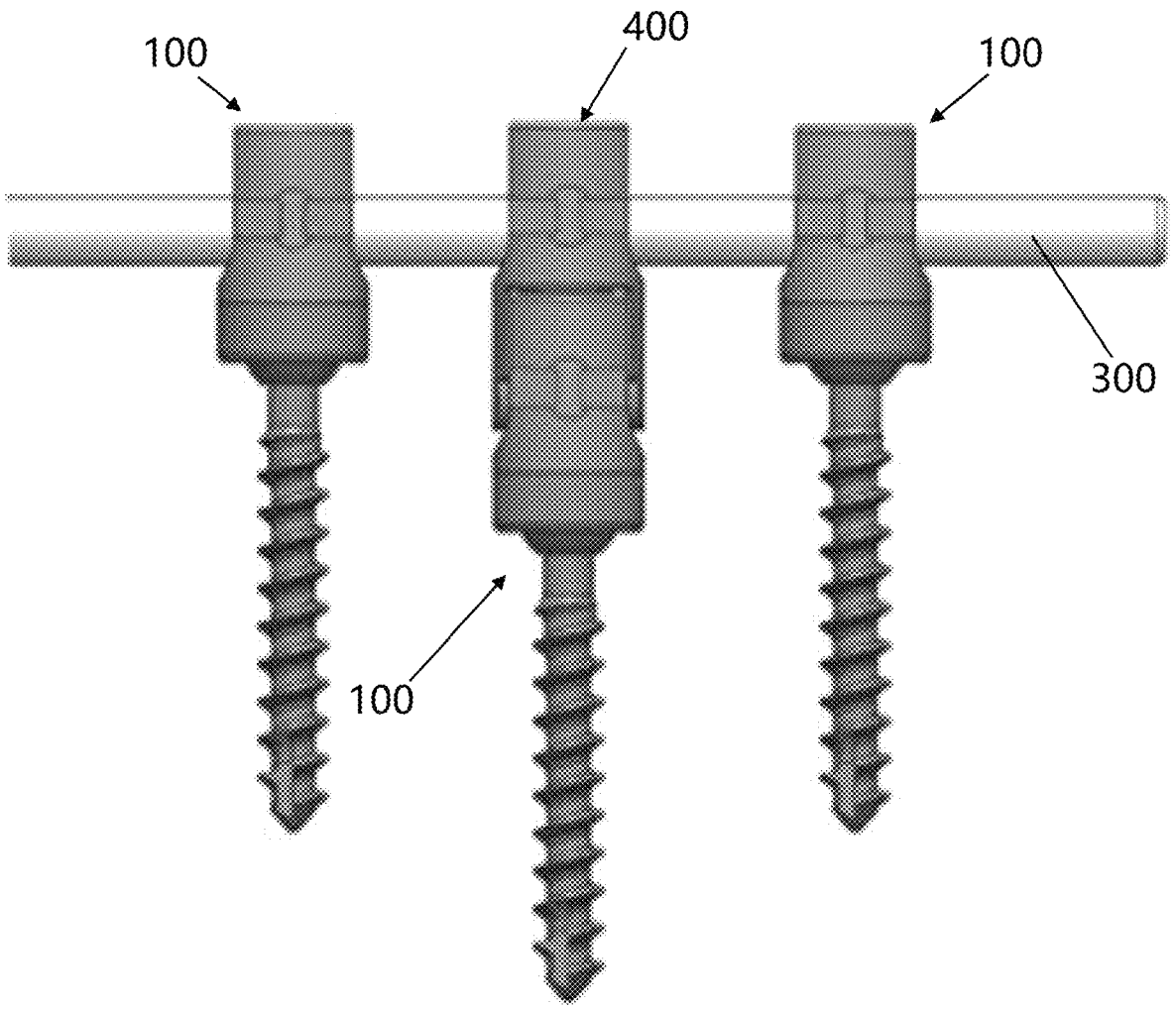
FIG. 8 is an illustration of the use of the orthopedic screw extension in accordance the present disclosure in a non-limiting application of securing the orthopedic screw extension to an orthopedic rod.

After an orthopedic rod 300 is inserted into first and second top side openings 440, 450 as illustrated in FIG. 8, a locking, similar to locking screw 150 of FIG. 1, can be inserted into top opening 520 in top cavity 500 and threadedly connect to threaded surface 510 on the inner surface of upwardly extending arms 460, 470. Once the locking screw is secured to the top portion, orthopedic rod 300 located in first and second top side openings 440, 450 is entrapped in first and second top side openings 440, 450, and thus secured to top portion 420.

Figure 3:
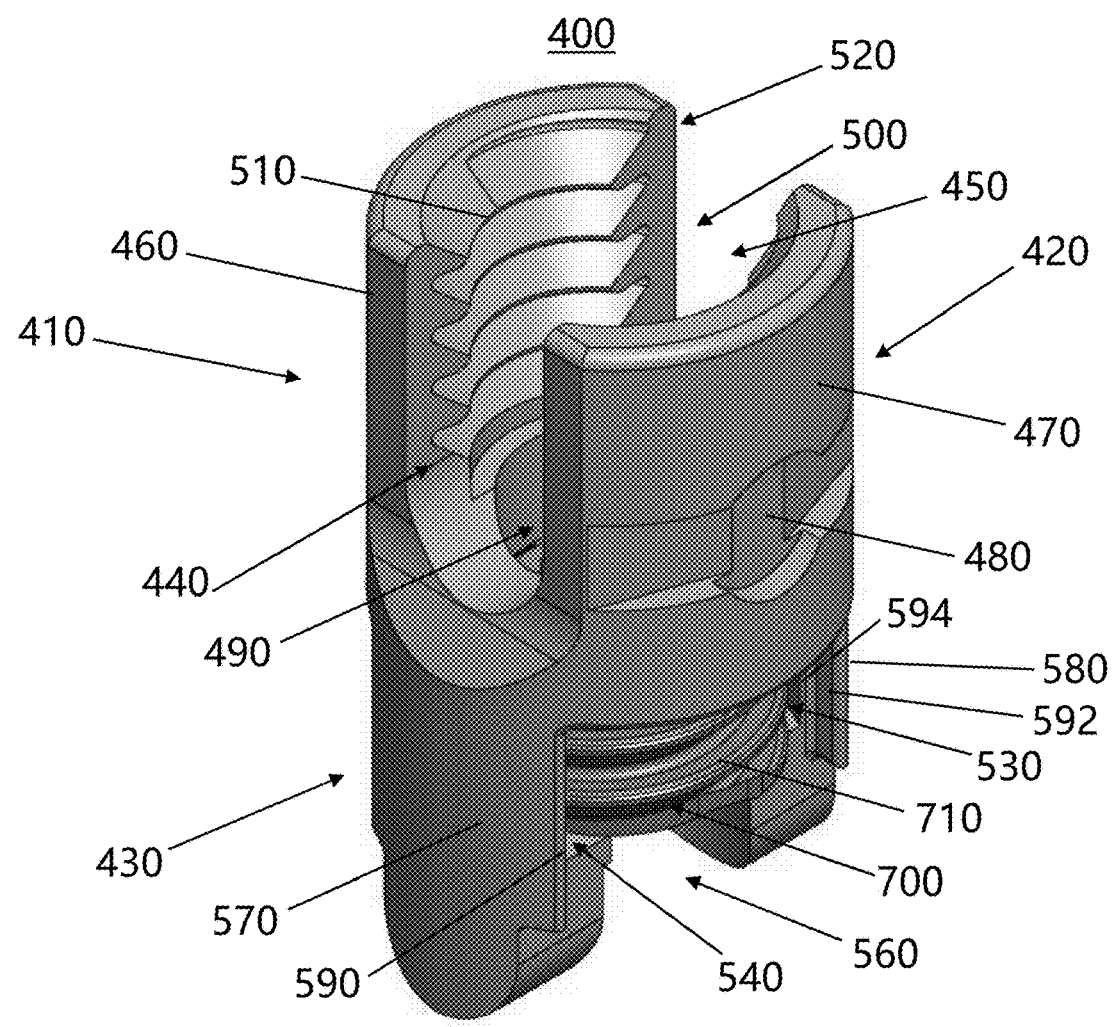
FIG. 3 is a front elevation view of a non-limiting orthopedic screw extension in accordance the present disclosure.
Figure 4:
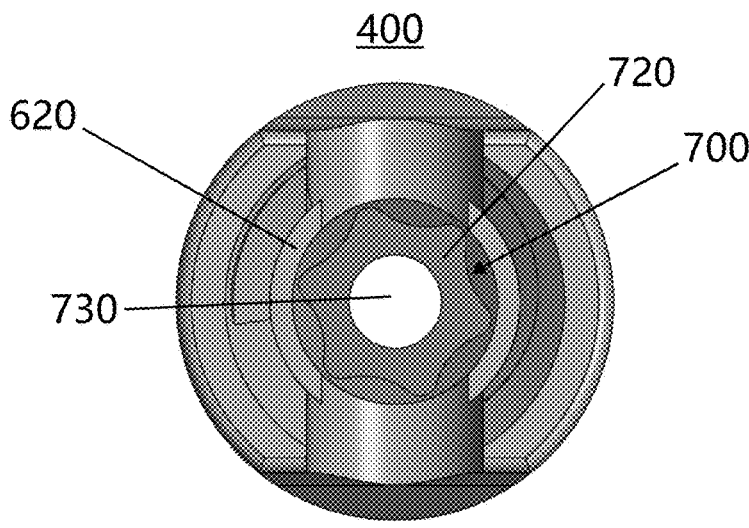
FIG. 4 is a top view of the orthopedic screw extension of FIG. 3.
Figure 5:
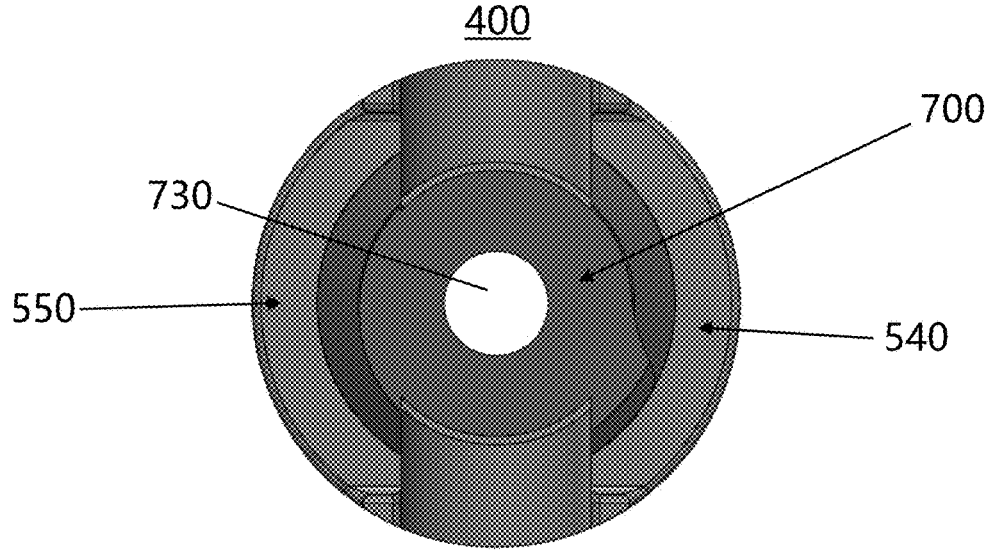
FIG. 5 is a bottom view of the orthopedic screw extension of FIG. 3.
Figure 7:
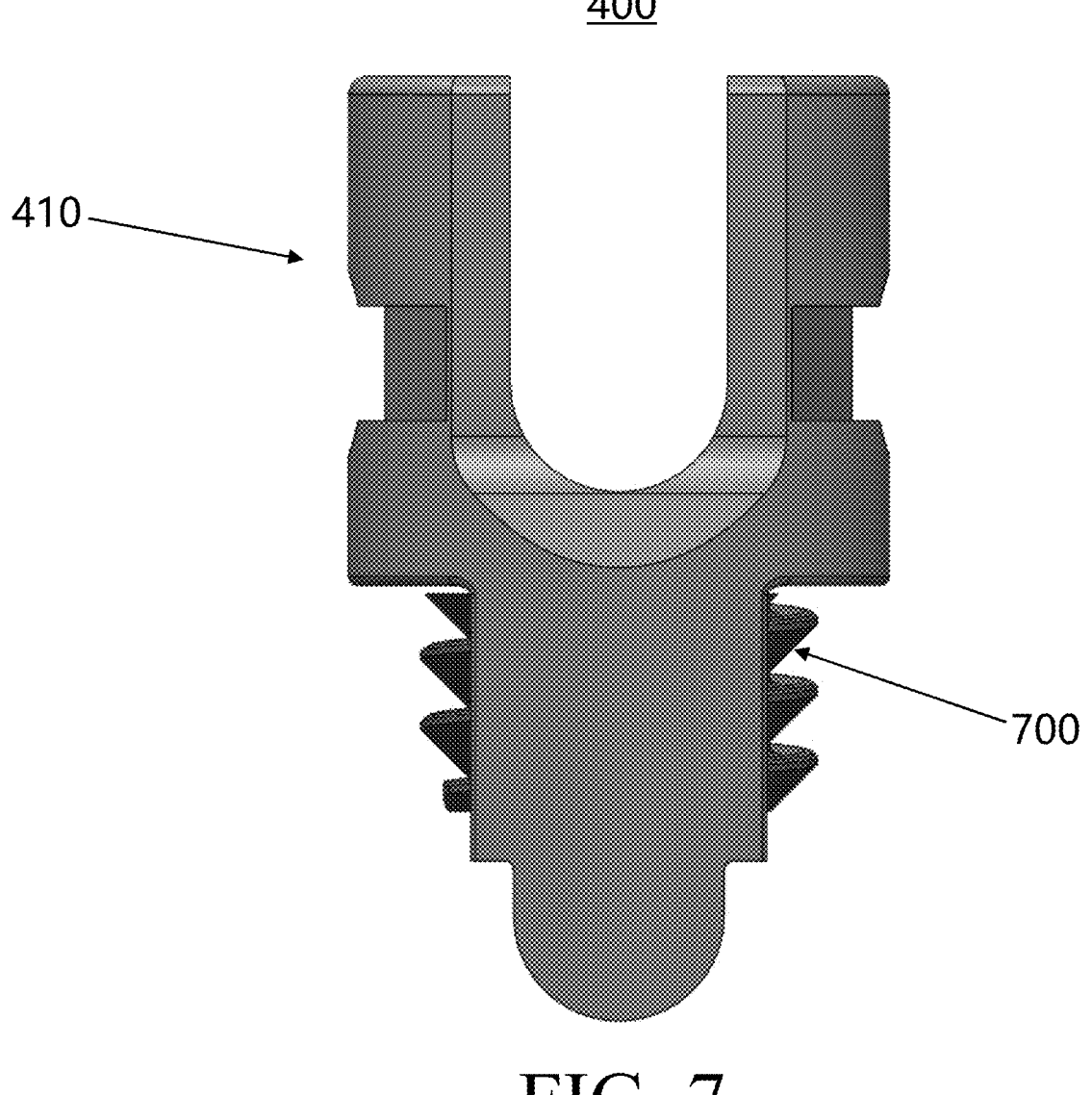
FIG. 7 is a side view of the orthopedic screw extension of FIG. 3.

As illustrated in FIGS. 3 and 7, the first and second top side openings 440, 450 have a generally U-shaped configuration; however; other shapes can be used (e.g., triangular, square, rectangular, polygonal, oval, etc.). The size and shape of first and second top side openings 440, 450 is generally the same.

The outer surface of body 410 can optionally include one or more slots and/or grooves 480. The one or more slots and/or grooves generally do not penetrate fully through body 410. The size and shape of the one or more slots and/or grooves is non-limiting.

Body 410 includes a mid-opening 490 that is positioned fully in top portion 420, or fully in bottom portion 430, or partially in the top and bottom portions of body 410 of orthopedic screw extension 400. Mid-opening 490 is generally positioned about the central axis of body 410. The cross-sectional shape of mid-opening 490 is generally circular. Mid-opening 490 forms a passageway between top cavity 500 and bottom cavity 530. Bottom portion 430 of body 410 includes a bottom cavity 530 that is located below the mid-opening 490 of body 410. The cross-sectional shape of bottom cavity 530 is generally circular; however, other shapes can be used.

The side of bottom portion 430 includes first and second bottom side openings 540, 550. First and second bottom side openings 540, 550 are configured to receive upwardly extending flanges 222, 224 of cylindrical head 220 of fixed head pedicle screw 200 when fixed head pedicle screw 200 is connected to bottom portion 430 of body 410 of orthopedic screw extension 400. As can be appreciated, first and second bottom side openings 540, 550 can also be configured to receive upwardly extending arms 460, 470 in top portion 420 of another orthopedic screw extension 400 when two orthopedic screw extensions 400 are connected together.

First and second bottom side openings 540, 550 are configured to be positioned on opposite sides of bottom cavity 530 and extend downwardly to bottom opening 560 of bottom cavity 530 of bottom portion 430. First and second bottom side openings 540, 550 in bottom portion 430 form two downwardly extending bottom arms 570, 580 in bottom portion 430. The longitudinal length of first and second bottom side openings 540, 550 generally extends 50-100% of the longitudinal length of bottom portion 430. First and second bottom side openings 540, 550 in bottom portion 430 have a generally U-shaped configuration; however; other shapes can be used (e.g., triangular, square, rectangular, polygonal, oval, etc.). The size and shape of first and second bottom side openings 540, 550 are generally the same; however, this is not required. Generally, less than 50% of first bottom side opening 540 is located directly beneath either first or second top side openings 440, 450 in top portion 420. Likewise, less than 50% of second bottom side opening 550 is located directly beneath either first second top side openings 440, 450. The central longitudinal axis of first bottom side opening 540 is illustrated to be about 85-95° off-center from the central longitudinal axis of first or second top side openings 440, 450 in top portion 420. Likewise, the central longitudinal axis of second bottom side opening 550 is illustrated to be about 85-95° off-center from the central longitudinal axis of first or second top side openings 440, 450 in top portion 420. Generally, first and second bottom side openings 540, 550 are positioned diametrically apart from one another about bottom cavity 530. Likewise, first or second top side openings 440, 450 in to top portion 420 are positioned diametrically apart from one another about top cavity 500. In one non-limiting embodiment, most (e.g., 55-99.99% and all values and ranges therebetween) or all of the longitudinal length of the inner surface of two downwardly extending bottom arms 570, 580 in bottom portion 430 is absent threading.

The maximum width of first bottom side opening 540 of bottom portion 430 is generally greater than the maximum width of either of first or second top side openings 440, 450 in top portion 420. Likewise, the maximum width of second bottom side opening 550 of bottom portion 430 is generally greater than the maximum width of either first or second top side openings 440, 450 in top portion 420. The size and width of first and second bottom side openings 540, 550 are generally the same.

Figure 6:
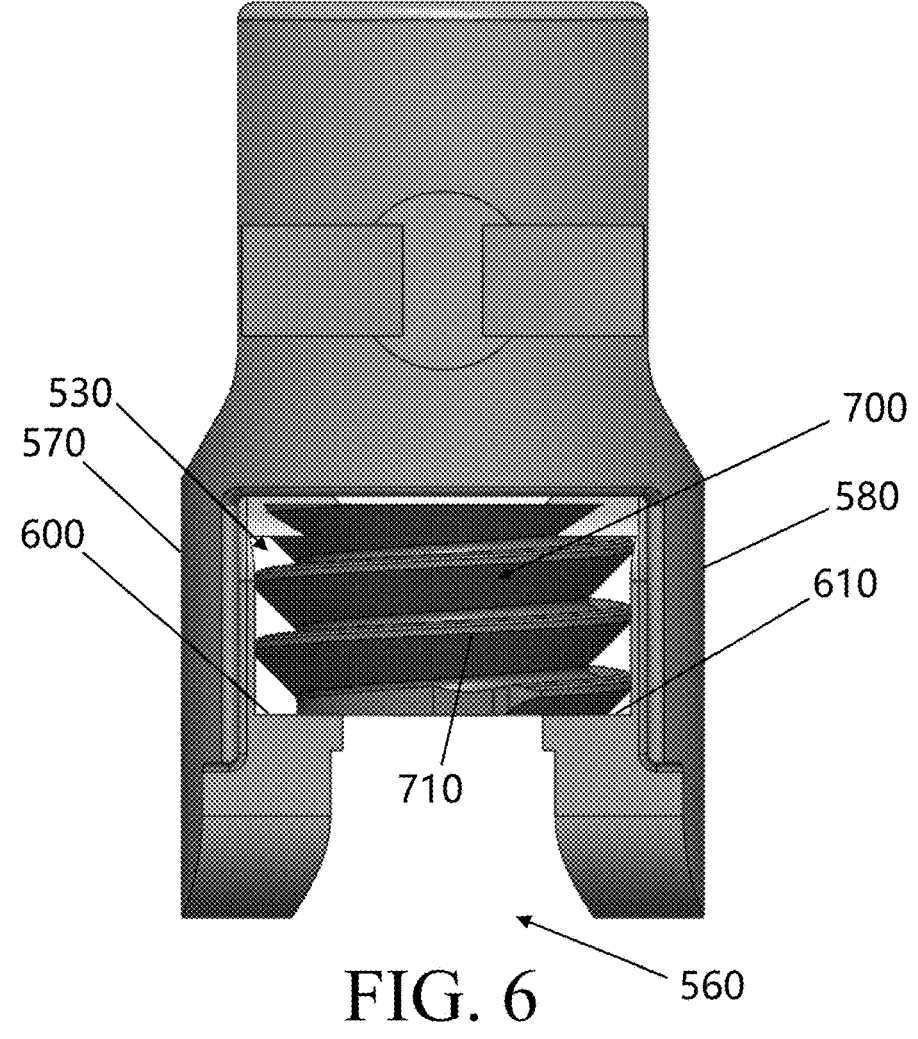
FIG. 6 is a front end view of the orthopedic screw extension of FIG. 3.

Bottom portion 430 includes first and second retention flanges 600, 610 on the interior surface of bottom cavity 430 and are located at and/or near the bottom end of bottom cavity 430. The retention flanges 600, 610 are configured to maintain the connecting member 700 in position within body 410 of orthopedic screw extension 400. As illustrated in FIG. 6, connecting member 700 is partially or fully positioned in bottom cavity 530. A top region of bottom portion 430 can optionally include one or more top retention flanges 620 configured to maintain connecting member 700 in position within body 410 of orthopedic screw extension 400.

Connecting member 700 is configured to be rotatable within body 410 of orthopedic screw extension 400. Connecting member 700 includes outer threading 710 that is configured to threadedly engage the threads on the inner surface of the pair of upwardly extending flanges 222, 224 of cylindrical head 220 of fixed head pedicle screw 200 to thereby secure fixed head pedicle screw 200 to bottom portion 430 of body 410 of orthopedic screw extension 400. Connecting member 700 is configured to maintain its position along the longitudinal axis of body 410 when connecting member 700 is rotated.

The top portion of connecting member 700 generally includes a non-circular-shaped recess or extended member 720 that can be engaged with a tool to rotate connecting member 700. Connecting member 700 can optionally include a central passageway 730 through connecting member 700 that is configured to enable a tool to be inserted through central passageway 730 to allow a user to engage a structure on fixed head pedicle screw 200 and rotate fixed head pedicle screw 200 while orthopedic screw extension 100 is positioned on and/or connected to fixed head pedicle screw 200.

The inner surface of the two downwardly extending bottom arms 570, 580 in bottom portion 430 can be configured to fit in the regions between the pair of upwardly extending flanges 222, 224 of fixed head pedicle screw 200. As illustrated in FIGS. 3, 6 and 7, the bottom region of bottom portion 430 of body 410 is curved and has a shape that can closely match the curved profile at the bottom of the regions between the pair of upwardly extending flanges 222, 224 of fixed head pedicle screw 200. The inner surface of bottom portion 430 of body 410 of orthopedic screw extension 400 can be shaped and sized to slide in the regions between the pair of upwardly extending flanges 222, 224 of fixed head pedicle screw 200. The length of the two downwardly extending bottom arms 570, 580 can be selected such that the bottom of the two downwardly extending bottom arms 570, 580 engages the bottom of the region between the pair of upwardly extending flanges 222, 224 of fixed head pedicle screw 200 when orthopedic screw extension 400 is connected to fixed head pedicle screw 200.

Bottom portion 430 of body 410 of orthopedic screw extension 400 can optionally include side extensions 590, 592 that are configured to overlie a portion of the outer surface of upwardly extending flanges 222, 224 of fixed head pedicle screw 200 when orthopedic screw extension 400 is connected to fixed head pedicle screw 200. Side extensions 590, 592 can be positioned on one or both sides of one or both of upwardly extending flanges 222, 224.

The inner surface of the bottom portion can include one or more inwardly extending flanges 594 that are configured to be positioned between one or both of upwardly extending flanges 222, 224 when orthopedic screw extension 400 is connected to fixed head pedicle screw 200. The use and/or shape side extensions 590, 592 and/or one or more inwardly extending flanges 594 on bottom portion 430 can be used to facilitate in a) the proper positioning of orthopedic screw extension 400 on the top portion of fixed head pedicle screw 200, b) reduce movement of orthopedic screw extension 100 relative to the top portion of fixed head pedicle screw 200 when orthopedic screw extension 100 is connected to fixed head pedicle screw 200, c) form an improved rigid connection between orthopedic screw extension 100 and the top portion of fixed head pedicle screw 200 when orthopedic screw extension 100 is connected to fixed head pedicle screw 200, and/or d) form a stronger connection between orthopedic screw extension 100 and the top portion of fixed head pedicle screw 200 when orthopedic screw extension 100 is connected to fixed head pedicle screw 200.

Orthopedic screw extension 400 in accordance with the present disclosure can be configured to enable orthopedic screw extension 400 to be adjustable in height when connected to the top portion of fixed head pedicle screw 200. Such a feature is advantageous in that orthopedic screw extension 400 can be adjusted to the desired height for a particular application, thereby reducing stress on the bone and/or orthopedic structures when attached to the bone of a patient. Such adjust can be by use of connecting member 700 that is located in body 410 of orthopedic screw extension 400. The amount that connecting member 700 is threaded into the top portion of fixed head pedicle screw 200 can be used to adjust the length of the extension formed by orthopedic screw extension 400.

Body 410 of orthopedic screw extension 400 can be formed of a variety of materials such as, but not limited to, stainless steel, cobalt chromium alloy, TiAl alloy, rhenium containing alloy, or a refractory metal alloy.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall therebetween.

To aid the Office and any readers of this application and any resulting patent in interpreting the claims appended hereto, Applicant does not intend any of the appended claims or claim elements to invoke 35 U.S.C. 112(f) unless the words "means for" or "step for" are explicitly used in the particular claim.

What is claimed:

1. An orthopedic screw extension that is configured to connect to an orthopedic screw and an orthopedic rod; said orthopedic screw extension comprising a body that has a top portion and a bottom portion; said top portion includes a top cavity; said bottom portion includes a bottom cavity; said top portion includes first and second top side openings that are configured to receive a portion of the orthopedic rod; said first and second top side openings form first and second upwardly extending arms; said top cavity includes a top securing surface that is configured to receive a rod connector to entrap the orthopedic rod in said first and second top side openings; said bottom cavity has first and second bottom side openings configured to receive a portion of a top portion of the orthopedic screw; said first and second bottom side openings form first and second downwardly extending arms; said first and second downwardly extending arms spaced from one another; at least a portion of said bottom cavity is located between said first and second downwardly extending arms; an inner surface of said first and second downwardly extending arms each include an inwardly extending flange; said inwardly extending flange on each of said first and second downwardly extending arms are spaced from one another; said inwardly extending flange on each of said first and second downwardly extending arms are spaced from a side edge of said respective first and second downwardly extending arms; said bottom cavity is located between said extending flange on each of said first and second downwardly extending arms; each of said inwardly extending flanges is configured to engage a side surface of a slot in a head portion of the pedicle screw and at least partially extend into the slot in the head portion when said orthopedic screw extension is connected to the pedicle screw; said bottom cavity extends fully through said bottom portion of said body of said orthopedic screw extension; said body includes a connecting member that is located between top and bottom ends of said body; said connecting member is movable relative to said body; said connecting member is configured to connect to the top portion of the orthopedic screw to thereby secure said orthopedic screw extension to the top portion of the orthopedic screw.

2. The orthopedic screw extension as defined in claim 1, wherein said top securing surface includes a threaded surface.

3. The orthopedic screw extension as defined in claim 1, wherein said body includes a mid-opening that is positioned along a longitudinal axis of said body; said mid-opening forms a passageway between said top cavity of said top portion and said bottom cavity of said bottom portion; said connecting member is entrapped in said bottom cavity.

4. The orthopedic screw extension as defined in claim 1, wherein a) said first and second bottom side openings are positioned on opposite sides of said bottom cavity, and/or b) said first and second top side openings are positioned on opposite sides of said top cavity.

5. The orthopedic screw extension as defined in claim 1, wherein a) less than 50% of said first bottom side opening is located directly beneath either the first and second top side openings in the top portion, and/or b) less than 50% of said second bottom side opening is located directly beneath either said first and second top side openings.

6. The orthopedic screw extension as defined in claim 1, wherein a) a maximum width of said first bottom side opening of said bottom portion is greater than a maximum width of either of said first or second top side openings in said top portion, and/or b) a maximum width of said second bottom side opening of said bottom portion is greater than a maximum width of either of said first or second top side openings in said top portion.

7. The orthopedic screw extension as defined in claim 1, wherein each said first and second downwardly extending arms of said bottom portion include first and second side retention flanges first and second side retention flanges on each of said first and second downwardly extending arms are configured to engage an outer surface of the orthopedic screw when said orthopedic screw extension is connected to the orthopedic screw.

8. The orthopedic screw extension as defined in claim 1, wherein said connecting member is rotatable within said body.

9. The orthopedic screw extension as defined in claim 1, wherein said connecting member includes an opening fully through a longitudinal axis of said connecting member.

10. An orthopedic screw assembly comprising:
an orthopedic screw arrangement that includes a threaded portion for implantation into a bone and a head portion that includes two side slots in the head portion that form two upwardly extending flanges;
an orthopedic rod; and
an orthopedic screw extension that is configured to connect to said orthopedic screw arrangement and said orthopedic rod; said orthopedic screw extension comprising a body that has a top portion and a bottom portion; said top portion includes a top cavity; said bottom portion includes a bottom cavity; said top portion includes first and second top side openings that are configured to receive a portion of the orthopedic rod; said first and second top side openings form first and second upwardly extending arms; said top cavity includes a top securing surface that is configured to receive a rod connector to entrap the orthopedic rod in said first and second top side openings; said bottom cavity has first and second bottom side openings configured to receive a portion of a top portion of said orthopedic screw arrangement; said first and second bottom side openings form first and second downwardly extending arms; said first and second downwardly extending arms spaced from one another; at least a portion of said bottom cavity is located between said first and second downwardly extending arms; a) an inner surface of said first and second downwardly extending arms of said bottom portion of said orthopedic screw extension each include an inwardly extending flange; said inwardly extending flange on each of said first and second downwardly extending arms are spaced from one another; said inwardly extending flange on each of said first and second downwardly extending arms are spaced from a side edge of said respective first and second downwardly extending arms; said bottom cavity is located between said extending flange on each of said first and second downwardly extending arms; each of said inwardly extending flanges is configured to engage a side surface of a slot in a head portion of said orthopedic screw arrangement and at least partially extend into the slot in the head portion when said orthopedic screw extension is connected to said orthopedic screw arrangement; said bottom cavity extends fully through said bottom portion of said body of said orthopedic screw extension; said body includes a connecting member that is located between top and bottom ends of said body; said connecting member is movable relative to said body; said connecting member is configured to connect to the top portion of said orthopedic screw arrangement to thereby secure said orthopedic screw extension to the top portion of said orthopedic screw arrangement; and a rod connector that is configured to connect to said top portion of said body and to entrap said orthopedic rod in said first and second top side openings.

11. The orthopedic screw assembly as defined in claim 10, wherein said body of said orthopedic screw extension includes a mid-opening that is positioned along a longitudinal axis of said body; said mid-opening forms a passageway between said top cavity of said top portion and said bottom cavity of said bottom portion; said connecting member is entrapped in said bottom cavity.

12. The orthopedic screw assembly as defined in claim 10, wherein each said first and second downwardly extending arms of said bottom portion of said orthopedic screw extension include first and second side retention flanges; said first and second side retention flanges on each of said first and second downwardly extending arms are is configured to engage an outer surface of said orthopedic screw arrangement when said orthopedic screw extension is connected to said orthopedic screw arrangement.

13. A method of treating a bone comprising:

providing an orthopedic screw arrangement; said orthopedic screw arrangement includes a threaded portion for implantation into the bone and a head portion that includes two side slots in said head portion that form two upwardly extending flanges;

providing an orthopedic rod;

providing an orthopedic screw extension; said orthopedic screw extension is configured to connect to said orthopedic screw arrangement and said orthopedic rod; said orthopedic screw extension comprising a body that has a top portion and a bottom portion; said top portion includes a top cavity; said bottom portion includes a bottom cavity; said top portion includes first and second top side openings that are configured to receive a portion of the orthopedic rod; said first and second top side openings form first and second upwardly extending arms; said top cavity includes a top securing surface that is configured to receive a rod connector to entrap the orthopedic rod in said first and second top side openings; said bottom cavity has first and second bottom side openings configured to receive a portion of a top portion of said orthopedic screw arrangement; said first and second bottom side openings form first and second downwardly extending arms; said first and second downwardly extending arms spaced from one another; at least a portion of said bottom cavity is located between said first and second downwardly extending arms; a) an inner surface of said first and second downwardly extending arms of said bottom portion of said orthopedic screw extension each include an inwardly extending flange; said inwardly extending flange on each of said first and second downwardly extending arms are spaced from one another; said inwardly extending flange on each of said first and second downwardly extending arms are spaced from a side edge of said respective first and second downwardly extending arms; said bottom cavity is located between said extending flange on each of said first and second downwardly extending arms; each of said inwardly extending flanges is configured to engage a side surface of a slot in a head portion of said orthopedic screw arrangement and at least partially extend into the slot in the head portion when said orthopedic screw extension is connected to said orthopedic screw arrangement; said bottom cavity extends fully through said bottom portion of said body of said orthopedic screw extension; said body includes a connecting member that is located between top and bottom ends of said body; said connecting member is movable relative to said body; said connecting member is configured to connect to the top portion of said orthopedic screw arrangement to thereby secure said orthopedic screw extension to the top portion of said orthopedic screw arrangement;

connecting said threaded portion of said orthopedic screw arrangement to the bone;

connecting said bottom portion of said body of said orthopedic screw extension to a portion of said head portion of said orthopedic screw arrangement; and connecting said orthopedic rod to said top portion of said body of said orthopedic screw extension.

14. The method as defined in claim 13, wherein said body of said orthopedic screw extension includes a mid-opening that is positioned along a longitudinal axis of said body; said mid-opening forms a passageway between said top cavity of said top portion and said bottom cavity of said bottom portion; said connecting member is entrapped in said bottom cavity.

15. The method as defined in claim 13, wherein each said first and second downwardly extending arms of said bottom portion of said orthopedic screw extension include first and second side retention flanges; said first and second side retention flanges on each of said first and second downwardly extending arms are is configured to engage an outer surface of said orthopedic screw arrangement when said orthopedic screw extension is connected to said orthopedic screw arrangement.

* * * * *